United States Patent [19]

Kamuro et al.

[11] Patent Number: 5,776,860
[45] Date of Patent: Jul. 7, 1998

[54] PLANT GROWTH PROMOTER

[75] Inventors: Yasuo Kamuro, Ichinomiya; Shinichi Hirakawa, Fujisawa; Hiroshi Fujisawa, Kawasaki, all of Japan

[73] Assignee: Nippon Zeon Co., Ltd., Tokyo, Japan

[21] Appl. No.: 507,453

[22] PCT Filed: Feb. 25, 1994

[86] PCT No.: PCT/JP94/00303

§ 371 Date: Aug. 25, 1995

§ 102(e) Date: Aug. 25, 1995

[87] PCT Pub. No.: WO94/18833

PCT Pub. Date: Sep. 1, 1994

[30] Foreign Application Priority Data

| Feb. 26, 1993 | [JP] | Japan | 5-063324 |
| Feb. 26, 1993 | [JP] | Japan | 5-063325 |
| Feb. 26, 1993 | [JP] | Japan | 5-063326 |

[51] Int. Cl.$^6$ .................................. A01N 37/00
[52] U.S. Cl. .................................. 504/313; 504/320
[58] Field of Search .................................. 504/313, 320

[56] References Cited

U.S. PATENT DOCUMENTS 3,998,967  12/1976  Weil .................................. 424/316

FOREIGN PATENT DOCUMENTS

| 0036106 | 9/1981 | European Pat. Off. . |
| 215928 | 11/1984 | European Pat. Off. . |
| 221059 | 4/1985 | European Pat. Off. . |
| 241821 | 1/1987 | European Pat. Off. . |
| 0274369 | 9/1990 | European Pat. Off. . |
| 0387165 | 9/1990 | European Pat. Off. . |
| 441764A | 8/1991 | European Pat. Off. . |
| 0509346 | 10/1992 | European Pat. Off. . |
| 0290416 | 6/1993 | European Pat. Off. . |
| 0597488 | 5/1994 | European Pat. Off. . |
| 276025 | 2/1990 | Japan . |
| 2230955 | 11/1990 | United Kingdom . |
| WO9212637 | 8/1992 | WIPO . |

OTHER PUBLICATIONS

Random House College Dictionary, p. 71 (1975).
Miersch et al. C.A. vol. 103 (1985) 103:33499t.
Dathe et al. C.A. vol. 107(1987) 107:91910p.
Chemical Abstracts, vol. 101, No. 11, 1984, Columbus, Ohio, abstract No. 85701f, "Improving soybean plant productivity," & BR 8 305 602 A (Akademie Der Wissenschaften Der DDR) 15 May 1984.

*Primary Examiner*—Allen J. Robinson
*Attorney, Agent, or Firm*—Sherman and Shalloway

[57] ABSTRACT

The present invention provides plant growth promoters each comprising, as an active ingredient, a jasmonic acid derivative represented by the following formula:

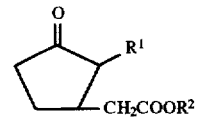

wherein $R^1$ represents a pentyl group or a pentenyl group and $R^2$ represents a hydrogen atom or an alkyl group. These promoters exhibit excellent growth promotion effects particularly on root vegetables, potatoes (tuber crops), cereals, fruit vegetables, fruit trees, flowers and ornamental plants and industrial crops.

13 Claims, No Drawings

PLANT GROWTH PROMOTER

DESCRIPTION

This application is a 371 of PCT/JP94/00303, filed Feb. 25, 1994.

[Technical Field]

The present invention relates to a plant growth promoter. More particularly, the present invention relates to a plant growth promoter applied to root vegetables, potatoes (tuber crops), cereals, fruit vegetables, fruit trees, flowers and ornamental plants, industrial crops, etc.

[Background Art]

Promotion of ordinary growth and development of crops for their increased production has been a big task in the agricultural technology. This task is becoming more important because food shortage on global scale is anticipated in the future.

The method for achieving the task includes a method by a technique employing an agricultural facility capable of controlling the temperature, light, etc. applied. This method, however, has had problems in that the facility and equipment therefor are required and that the method has a limitation as compared to the labor needed for said control.

Meanwhile, there have recently been made attempts of isolating a physiologically active substance from plant tissue samples and studying its effect on the life cycle (germination, growth, blooming, bearing and aging) of plants in order to promote their growth and development for increased production. However, the number of cases is very small yet in which a physiologically active substance having a plus effect on the growth and development of plants has been put into practical use. Moreover, the number of substances is also very small which can exhibit a growth promotion action on plants in their actual outdoor cultivation.

Under the above situation, the present inventors made an extensive study and, as a result, found out that certain jasmonic acid derivatives have a growth promotion action on plants. The finding has led to the completion of the present invention.

[Disclosure of the Invention]

According to the present invention there is provided a plant growth promoter comprising, as an active ingredient, a jasmonic acid derivative represented by the following formula:

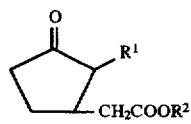

(1)

wherein $R^1$ represents a pentyl group or a pentenyl group and $R^2$ represents a hydrogen atom or an alkyl group.

According to the present invention there is also provided a plant growth promoter comprising, as active ingredients, a jasmonic acid derivative and a brassinosteroid.

The jasmonic acid derivative represented by the formula (1), according to the present invention is restricted to those jasmonic acid derivatives wherein $R^1$ is a pentyl group or a pentenyl group and $R^2$ is a hydrogen atom or an alkyl group. The pentenyl group is preferably 2-pentenyl group. The alkyl group is exemplified by methyl group, ethyl group, propyl group, isopropyl group, butyl group, isobutyl group, pentyl group, hexyl group, heptyl group, octyl group, nonyl group and decanyl group. $R^2$ is preferably an alkyl group of 2–6 carbon atoms, particularly preferably an alkyl group of 3 or 4 carbon atoms.

Each of these jasmonic acid derivatives is a known compound and can be produced by an ordinary process. For example, a dihydrojasmonic acid derivative which is a jasmonic acid derivative of formula (1) having a pentyl group as $R^1$ and an alkyl group of 1–10 carbon atoms as $R^2$, can be obtained by subjecting, to Michael addition, 2-pentylcyclopentene-1-one and an alkyl malonate and then subjecting the resulting adduct to decarboxylation.

The content of the jasmonic acid derivative in the plant growth promoter of the present invention cannot be specified in a general range because it varies depending upon the kind of plant to which said promoter is applied, the form, method and timing by and at which said promoter is used, etc. However, when the plant growth promoter is used in the form of a solution and by spraying, said content is controlled in a concentration of generally 0.01–500 ppm, preferably 0.05–300 ppm, more preferably 0.1–200 ppm.

When the concentration is outside the above range, the concentration is not economical; the growth promotion effect of the present promoter is not expressed in some cases; and even the growth inhibition effect is expressed in some cases.

The growth promoter of the present invention comprises a jasmonic acid derivative as an active ingredient and, besides the jasmonic acid derivative, can comprise auxiliary agents ordinarily used, such as carrier, emulsifier, dispersing agent, spreading agent, wetting and spreading agent, sticking agent, disintegrating agent and the like.

The carrier can be exemplified by liquid carriers such as water, alcohol (e.g. ethanol, methanol, isopropanol, butanol, ethylene glycol and propylene glycol), ketone (e.g. acetone, methyl ethyl ketone and cyclohexanone) and ester (e.g. ethyl acetate); and solid carriers such as talc, bentonite, clay, kaolin, diatomaceous earth, vermiculite, slaked lime, siliceous sand, ammonium sulfate, urea and the like.

As the emulsifier or dispersing agent, there is generally used a surfactant such as anionic surfactant (e.g sodium higher alcohol sulfate), cationic surfactant (e.g. stearyltrimethylammonium chloride), nonionic surfactant (e.g. polyoxyethylene alkylphenyl ether) or the like.

There is no particular restriction as to the form in which the present growth promoter is used. The form includes emulsion, suspension, powder, water-dispersible powder, water-soluble powder, granules, paste, aerosol, etc.

The timing and method at and in which the growth promoter of the present invention is used, are not necessarily definite; generally, however, said growth promoter is used, for example, by spraying or coating said growth promoter on a plant in the growth and development stage, or by dipping seeds of a plant in said growth promoter.

The plant growth promoter of the present invention can exhibit an excellent growth promotion effect even when comprising, as the active ingredient, only a jasmonic acid derivative of formula (1), but can exhibit a further superior growth promotion effect when comprising said jasmonic acid derivative in combination with a brassinosteroid.

The brassinosteroid is a group of compounds each known as a plant growth promotion substance and includes, for example, brassinolide, epibrassinolide, homobrassinolide, dolicholide and castasterone. Preferable of these are brassinolide, epibrassinolide and homobrassinolide.

The content of the brassinosteroid in the present plant growth promoter cannot be specified in a general range because it varies depending upon the kind of plant to which said promoter is applied, the form, method and timing by and at which said promoter is used, etc. However, when the plant growth promoter is used in the form of a solution and by spraying, said content is controlled in a concentration of generally 0.00001-0.1 ppm, preferably 0.0001-0.05 ppm, more preferably 0.001-0.05 ppm.

In the present invention, a synergistic plant growth promotion effect is obtained by using a brassinosteroid in combination.

[Industrial Applicability]

The growth promoter of the present invention exhibits a growth promotion action to extensive plants including root vegetables, potatoes (tuber crops), cereals, fruit vegetables, fruit tress, flowers and ornamental plants and industrial crops. Some examples of the plants to which the present growth promoter can be applied, include root vegetables such as radish, carrot, onion, beat and the like; potatoes (tuber crops) such as potato, sweet potato, taro, cassava and the like; cereals such as rice, wheat, barley, oats, German millet, sawa millet, millet, corn, bean and the like; fruit vegetables such as cucumber, Japanese cantaloupe, strawberry, tomato, melon and the like; fruit trees such as citrus tree, apple, grape, peach and the like; flowers and ornamental plants such as lily, tulip, gladiolus, carnation, rose and the like; and industrial crops such as cotton, hemp, turf, stevia and the like. The examples are not restricted thereto. For example, grasses and trees are planted in a desert or a waste land for greening, in some cases; and the present plant growth promoter is applicable even to such grasses and trees.

The site of plant at which the effect of the present growth promoter is expressed, differs depending upon the kind of plant, but is, for example, leaf, stem, root, tuber, rhizome, fruit and flower bud. The growth promoter promotes growth of leaf, stem, root, tuber, rhizome, fruit, etc., inviting increases in length and weight. The growth promoter promotes differentiation of flower bud, inviting increases in germination rate, number of flowers, etc. The growth promoter has effects on fruit, such as increases in weight, succharose content and color level, and the like.

The effects of the present growth promoter differ slightly depending upon the structure of jasmonic acid derivative used and the kind of plant to which the promoter is applied.

Thus, the present invention can promote plant growth.

[Best Mode for Carrying Out the Invention]

The present invention is hereinafter described more specifically by way of Examples. In the following Examples and Comparative Examples, parts and % are each by weight unless otherwise specified.

EXAMPLE 1

(Growth promotion effect on early variety radish)

Emulsions containing 20% of a jasmonic acid derivative of the above-mentioned formula (1) wherein $R^1$ and $R^2$ are each a substituent shown in Table 1, were prepared using a mixed solution of xylol:isophorone polyoxyethylene alkylphenyl ether=60:20:20. Each emulsion was adjusted with water so as to contain the jasmonic acid derivative in a concentration of 0.5 ppm, to prepare test solutions.

A radish (early variety: Akamaru-Commet) was cultivated in the conventional manner in an outdoor farm. When the root began to thicken, the test solutions were sprayed in an amount of 10 liters per are (100 m$^2$) of cultivation area.

16 days after the spraying, 15 plants each of good growth and development were harvested from each test plot and measured for weight of leaf portion and weight of root portion to calculate respective relative values (%) to non-treated test plot. The results are shown in Table 1.

TABLE 1

| No. | $R^1$ | $R^2$ | Relative leaf weight (%) | Relative root weight (%) |
|---|---|---|---|---|
| Present invention | | | | |
| 1-1 | —$C_5H_{11}$ | —$CH_3$ | 108 | 110 |
| 1-2 | —$C_5H_{11}$ | —$C_2H_5$ | 104 | 110 |
| 1-3 | —$C_5H_{11}$ | —$C_3H_7$ | 111 | 119 |
| 1-4 | —$C_5H_{11}$ | —$CH(CH_3)2$ | 106 | 106 |
| 1-5 | —$C_5H_{11}$ | —$C_4H_9$ | 107 | 118 |
| 1-6 | —$C_5H_{11}$ | —$C_6H_{13}$ | 107 | 107 |
| 1-7 | —$CH_2CH=CHC_2H_5$ | —$CH_3$ | 108 | 108 |
| 1-8 | —$CH_2CH=CHC_2H_5$ | —$CH(CH_3)2$ | 104 | 109 |
| 1-9 | —$CH_2CH=CHC_2H_5$ | —$C_4H_7$ | 110 | 112 |
| 1-10 | —$CH_2CH=CHC_2H_5$ | —$C_4H_9$ | 108 | 110 |
| Comparison | | | | |
| 1-11 | Non-treated test plot (control) | | 100 | 100 |

EXAMPLE 2

(Growth promotion effect on potato when seed potatoes were treated)

Test solutions containing 100 ppm of a dihydrojasmonic acid derivative of the formula (1) wherein $R^1$ is a pentyl group and R2 is a substituent shown in Table 2, were prepared using a mixed solution of ether : water=70:30. Seeds of a potato (variety: May Queen) were momentarily dipped in the test solutions.

On the day after the dipping, the seeds were set in a farm (15 potatoes were set in one test plot) and cultivated in the conventional manner. 80 days after the setting, 10 plants of good growth and development were dug out from each test plot, and the number of potatoes of each plant was measured to determine the average potato number per plant. Also, the weight of potatoes of each plant was measured to determine the average potato weight per plant and calculate its relative value (%) to non-treated test plot. The results are shown in Table 2.

TABLE 2

| No. | | $R^2$ | Potato number | Relative potato weight (%) |
|---|---|---|---|---|
| Present invention | 2-1 | —$C_2H_5$ | 7.1 | 112 |
| | 2-2 | —$C_3H_7$ | 7.2 | 114 |
| | 2-3 | —$CH(CH_3)_2$ | 7.4 | 116 |
| | 2-4 | —$C_4H_9$ | 7.1 | 113 |
| | 2-5 | —$C_6H_{13}$ | 7.0 | 110 |
| | 2-6 | —$C_7H_{15}$ | 7.0 | 110 |
| | 2-7 | —$C_8H_{17}$ | 7.0 | 110 |
| Comparison | 2-8 | Non-treated test plot (control) | 5.8 | 100 |

EXAMPLE 3

(Growth promotion effect on potato when sprayed during growth and development stage)

Emulsions containing 20% of a dihydrojasmonic acid derivative of the formula (1) wherein $R^1$ is a pentyl group and $R^2$ is a substituent shown in Table 3, were prepared using a mixed solution of xylol: isophorone:polyoxyethylene alkylphenyl ether=60:20:20. Each emulsion was adjusted with water so as to contain the dihydrojasmonic acid derivative in a concentration of 10 ppm, to prepare test solutions.

Seeds of a potato (variety: May Queen) were set and cultured in the conventional manner. When the number of the true leaves became 5 to 6, the test solutions were sprayed on the plants in an amount of 10 liters per are (100 m$^2$) of cultivation area.

53 days after the spraying, 15 plants each of good growth and development were dug out from each test plot. Each plant was measured for number of potatoes to calculate the average potato number per plant. Also, the weight of potatoes of each plant was measured to determine the average potato weight per plant and calculate its relative value (%) to non-treated test plot.

The results are shown in Table 3.

TABLE 3

| No. | | R$^2$ | Potato number | Relative potato weight (%) |
|---|---|---|---|---|
| Present invention | 3-1 | —C$_2$H$_5$ | 6.3 | 108 |
| | 3-2 | —C$_3$H$_7$ | 6.3 | 108 |
| | 3-3 | —CH(CH$_3$)$_2$ | 6.6 | 111 |
| | 3-4 | —C$_4$H$_9$ | 6.7 | 113 |
| | 3-5 | —C$_6$H$_{13}$ | 6.5 | 110 |
| | 3-6 | —C$_7$H$_{15}$ | 6.4 | 109 |
| | 3-7 | —C$_8$H$_{17}$ | 6.4 | 109 |
| Comparison | 3-8 | Non-treated test plot (control) | 5.6 | 100 |

EXAMPLE 4
(Growth promotion effect on rice when rice seedlings were sprayed)

An emulsion containing 20% of propyl dihydrojasmonate [a compound of the formula (1) wherein R$^1$ is a pentyl group and R$^2$ is a propyl group] was prepared using a mixed solution of xylol : isophorone : polyoxyethylene alkylphenyl ether=60:20:20. The emulsion was adjusted with water so as to contain the propyl dihydrojasmonate in a concentration of 5 ppm, to prepare a test solution.

One day before the transplantation of 5- to 6-leaf seedlings of a rice (variety: Koshihikari), the test solution was sprayed in an amount of 10 liters per are so that the surface of each leaf got wet uniformly with the test solution. The sprayed seedlings were transplanted into pots (1/2,500 are) (3 seedlings per pot) and cultured outdoors in the conventional manner.

35 days after the transplantation, the number of tillers per seedling was measured and its relative value (%) to non-treated test plot was calculated. The relative value was 106%. At the time of harvesting, the number of ears per plant and the weight of ears per plant were measured, and the respective relative values (%) to non-treated test plot were calculated. The relative number of ears was 107% and the relative weight of ears was 109%.

EXAMPLE 5
(Growth promotion effect on wheat when wheat seeds were treated)

A test solution containing 10 ppm of propyl dihydrojasmonate [a compound of the formula (1) wherein R$^1$ is a pentyl group and R$^2$ is a propyl group] was prepared using a mixed solution of ethanol:water=50:50. Seeds of a wheat (variety: Nohrin No. 61) 25 were momentarily dipped in the test solution and then sowed into pots (15 cm in diameter and 15 cm in depth) by 20 grains per pot (one test plot consisted of two pots). Cultivation was conducted in outdoor natural conditions. Two months after the sowing, the growing plants were pulled out and measured for plant height, fresh weight and number of tillers, and the respective relative values (%) to non-treated test plot were calculated. The relative plant height was 110%; the relative fresh weight was 120%; and the relative number of tillers was 124%.

EXAMPLE 6
(Growth promotion effect on wheat when sprayed during growth and development stage)

An emulsion containing 20% of propyl dihydrojasmonate [a compound of the formula (1) wherein R$^1$ is a pentyl group and R$^2$ is a propyl group] was prepared using a mixed solution of xylol:isophorone:polyoxyethylene alkylphenyl ether=60:20:20. The emulsion was adjusted with water so as to contain the propyl dihydrojasmonate in a concentration of 10 ppm, to prepare a test solution.

Seeds of a wheat (variety: Nohrin No. 61) were sowed into pots (15 cm in diameter and 15 cm in depth) by 20 grains per pot (one test plot consisted of two pots). One month later (when tillering started), the test solution was sprayed uniformly in an amount of 10 liters per are.

Two months after the sowing, the growing plants were pulled out and measured for plant height, fresh weight and number of tillers, and the respective relative values (%) to non-treated test plot were calculated. The relative plant height was 110%; the relative fresh weight was 120%; and the relative number of tillers was 113%.

EXAMPLE 7
(Growth promotion effect on strawberry when sprayed during growth and development stage)

A test solution containing 10 ppm of propyl dihydrojasmonate [a compound of the formula (1) wherein R$^1$ is a pentyl group and R$^2$ is a propyl group] was prepared using a mixed solution of ethanol:water=50:50.

A strawberry (variety: Reikou) was cultivated in the conventional manner. One month after the harvesting, the test solution was uniformly sprayed in an amount of 10 liters per are. 6–10 days after the spraying, fruits were harvested; their average weight was measured; and its relative value (%) to non-treated test plot was calculated and was 110%.

EXAMPLE 8
(Growth promotion effect on grape when sprayed on fruits)

An emulsion containing 20% of propyl dihydrojasmonate [a compound of the formula (1) wherein R$^1$ is a pentyl group and R$^2$ is a propyl group] was prepared using a mixed solution of xylol : isophorone : polyoxyethylene alkylphenyl ether=60:20:20. The emulsion was adjusted with water so as to contain the propyl dihydrojasmonate in a concentration of 100 ppm, to prepare a test solution.

A grape (variety: Kyoho) having about 35–40 fruits per bunch, which was cultivated outdoors in the conventional manner, was used for this test. The test solution was uniformly sprayed on grape bunches when they began to color and maturation, in an amount of 10 ml per bunch (one test plot consisted of 5 bunches). 25 days after the spraying, harvesting was conducted, and the quality of fruits was examined and calculated as its relative value (%) to non-treated test plot.

The relative coloring degree was 149%; the relative Brix scale was 110%; and the relative acid content was 83%. Thus, the maturation of fruits was promoted.

The qualities of fruits were measured as follows.

Coloring degree:

The coloring degree of each bunch was expressed as a number between 0 (no coloring) and 10 (complete coloring), and the coloring degree average of individual bunches was calculated. This average was converted to its relative value to nontreated test plot.

Brix %: The Brix % of juice of each bunch was measured by the use of a refractometer, and the Brix % average of individual bunches was calculated. This average was converted to its relative value to nontreated test plot.

Acid content:

The amount of 0.1N NaOH necessary for neutralizing the juice of each bunch was measured, and the NaOH amount average of individual bunches was calculated.

This average was converted to its relative value to non-treated test plot.

EXAMPLE 9
(Growth promotion effect on cotton when cotton seeds were treated)

A test solution containing 50 ppm of propyl dihydrojasmonate [a compound of the formula (1) wherein $R^1$ is a pentyl group and $R^2$ is a propyl group] was prepared using a mixed solution of ethanol:water=50:50. Cotton seeds were momentarily dipped in the test solution, and 30 each of the resulting seeds were sowed in two test plots.

10 days after the sowing, the germination rate of seeds was measured and was 90%. Meanwhile, the germination rate of non-treated test plot was 70%.

One month after the sowing, 10 plants per test plot, of good growth and development were measured for average fresh weight. It was converted into its relative value (%) to non-treated test plot, which was 113%.

EXAMPLE 10
(Growth promotion effect on gramineous weed when its seeds were treated)

A test solution containing 20 ppm of propyl dihydrojasmonate [a compound of the formula (1) wherein $R^1$ is a pentyl group and $R^2$ is a propyl group] was prepared using a mixed solution of ethanol:water=50:50. In the test solution were momentarily dipped seeds (Bromus inermis, Mancha) of a typical gramineous weed commonly used for greening. The test solution-coated seeds were air-dried and sowed in an amount of 40 grains per test plot.

15 days after the sowing, the germination rate of seeds was measured and was 70%. Meanwhile, the germination rate of non-treated test plot was 51%.

24 days after the sowing, the plant height and total fresh weight of each test plot were measured and calculated as respective values (%) to non-treated test plot. The relative plant height was 110% and the relative total fresh weight was 115%.

EXAMPLE 11
(Growth promotion effect on tomato when sprayed during growth and development stage)

An emulsion containing 20% of a propyl dihydrojasmonate [a compound of the formula (1) wherein $R^1$ is a pentyl group and $R^2$ is a propyl group] was prepared using a mixed solution of xylol : isophorone : polyoxyethylene-alkylphenyl ether=60:20:20. The emulsion was adjusted with water so as to contain the propyl dihydrojasmonate in a concentration of 100 ppm, to prepare a test solution.

A tomato (variety: Momotaro) was cultured in the conventional manner in a polylvinyl chloride)-made house. When each of the first bunches reached a green mature stage, the above test solution was sprayed uniformly on the whole surfaces of fruits, stems and leaves in an amount of 100 ml per plant.

10–30 days after the spraying, harvesting was conducted; the average weight of fruits of first bunches was measured; and its relative value (%) to non-treated test plot was calculated and was 123%.

EXAMPLE 12
(Growth promotion effect on lily)

Using a mixed solution of ethanol:water=50:50, there were prepared solutions each containing 1% of a dihydrojasmonic acid derivative of the formula (1) wherein $R^1$ is a pentyl group and $R^2$ is a substituent shown in Table 4. Each solution was diluted with water so as to contain the dihydrojasmonic acid derivative in a concentration of 1 ppm, to prepare test solutions. Bulbs of a lily were dipped in the test solutions for 24 hours, after which they were set outdoors and subjected to conventional cultivation.

When blooming reached, the heights of plants were measured and their average was determined. The average plant height was converted to its relative value (%) to non-treated test plot. The results are shown in Table 4.

TABLE 4

| | No. | $R^2$ | Relative lily height (%) |
|---|---|---|---|
| Present invention | 12-1 | —CH(CH$_3$)$_2$ | 128 |
| | 12-2 | —C$_4$H$_9$ | 117 |
| Comparison | 12-3 | Non-treated test plot (control) | 100 |

EXAMPLE 13
(Growth promotion effect of jasmonic acid derivative and brassinosteroid on early variety radish when sprayed during growth and development stage)

Test solutions were prepared in the same manner as in Example 1 so that each solution contained a jasmonic acid derivative and/or El brassinosteroid in respective concentrations shown in Table 5.

A radish (early variety: Akamaru-Commet) was cultured in an outdoor farm in the conventional manner. When the root began to thicken, each test solution was sprayed on the growing plants in an amount of 10 liters per are of cultivation area.

16 days after the spraying, 15 plants of good growth and development were harvested from each test plot, and the weight of their roots was measured and its relative value (%) to non-treated test plot was calculated. The results are shown in Table 5.

A synergistic effect of a jasmonic acid derivative and a brassinosteroid was recognized from Table 5.

TABLE 5

| No. | Compound 1 (ppm) *1 | Compound 2 (ppm) *2 | Brassinolide (ppm) | Epibrassinolide (ppm) | Homobrassinolide (ppm) | Relative root weight (%) |
|---|---|---|---|---|---|---|
| 13-1 | 0.5 | | 0.01 | | | 136 |
| 13-2 | 0.5 | | | 0.01 | | 140 |
| 13-3 | 0.5 | | | | 0.01 | 132 |
| 13-4 | | 0.5 | 0.01 | | | 133 |
| 13-5 | | 0.5 | | 0.01 | | 134 |
| 13-6 | | 0.5 | | | 0.01 | 138 |
| 13-7 | 0.5 | | | | | 116 |
| 13-8 | | 0.5 | | | | 112 |
| 13-9 | | | 0.01 | | | 106 |
| 13-10 | | | | 0.01 | | 109 |
| 13-11 | | | | | 0.01 | 107 |
| 13-12 | | | | | | 100 |

In the above table, the blank squares each indicate zero.

*1: Compound 1 refers to a jasmonic acid derivative of formula (1) wherein $R^1$ is —C$_5$H$_8$ and $R^2$ is —(CH(CH$_3$)$_2$.

*2: Compound 2 refers to a jasmonic acid derivative of formula (1) wherein $R^1$ is —C$_5$H$_8$ and $R^2$ is —C$_4$H$_9$.

EXAMPLE 14

(Growth promotion effect of jasmonic acid derivative and brassinosteroid on potato when seed potatoes were treated)

Test solutions were prepared in the same manner as in Example 2 so that each solution contained a jasmonic acid derivative and/or a brassinosteroid in respective concentrations shown in Table 6. Seeds of a potato (variety: May Queen) were momentarily dipped in the test solutions.

One day after the dipping, the seed potatoes were set in a farm and subjected to conventional cultivation at a rate of 15 seed potatoes per test plot. 80 days after the setting, 10 plants of good growth and development were dug out from each test plot to measure the number of potatoes per plant and determine an average potato number per plant. Also, the weight of potatoes per plant was measured; an average potato weight per plant was determined; and its relative value (%) to non-treated test plot was calculated. The results are shown in Table 6.

A synergistic effect of a jasmonic acid derivative and a brassinosteroid was recognized from Table 6.

TABLE 6

| No. | Compound 1 (ppm) *1 | Compound 2 (ppm) *2 | Brass- inolide (ppm) | Epibrass- inolide (ppm) | Homobrass- inolide (ppm) | Relative potato weight (%) |
|---|---|---|---|---|---|---|
| 14-1 | 50 | | 0.01 | | | 135 |
| 14-2 | 50 | | | 0.01 | | 139 |
| 14-3 | 50 | | | | 0.01 | 130 |
| 14-4 | | 50 | 0.01 | | | 129 |
| 14-5 | | 50 | | 0.01 | | 128 |
| 14-6 | | 50 | | | 0.01 | 127 |
| 14-7 | 50 | | | | | 113 |
| 14-8 | | 50 | | | | 110 |
| 14-9 | | | 0.01 | | | 104 |
| 14-10 | | | | 0.01 | | 106 |
| 14-11 | | | | | 0.01 | 106 |
| 14-12 | | | | | | 100 |

In the above table, the blank squares each indicate zero.

*1: Compound 1 refers to a jasmonic acid derivative of formula (1) wherein $R^1$ is —$C_5H_8$ and $R^2$ is —$CH(CH_3)_2$.

*2: Compound 2 refers to a jasmonic acid derivative of formula (1) wherein $R^1$ is —$C_5H_8$ and $R^2$ is —$C_4H_9$.

EXAMPLE 15

(Growth promotion effect of jasmonic acid derivative and brassinosteroid on wheat when wheat seeds were treated)

Test solutions were prepared in the same manner as in Example 5 so that each solution contained a jasmonic acid derivative and/or a brassinosteroid in respective concentrations shown in Table 7. Seeds of a wheat (variety: Nohrin No. 61) were momentarily dipped in the test solutions and subjected to conventional cultivation. When the seeds reached a three-leaf age, 100 plants were pulled out from each test plot to measure an average fresh weight of individual plants and calculate its relative value (%) to non-treated test plot. The results are shown in Table 7.

A synergistic effect of a jasmonic acid derivative and a brassinosteroid was recognized from Table 7.

TABLE 7

| No. | Compound 1 (ppm) *1 | Compound 2 (ppm) *2 | Brass- inolide (ppm) | Epibrass- inolide (ppm) | Homobrass- inolide (ppm) | Relative fresh weight (%) |
|---|---|---|---|---|---|---|
| 15-1 | 5 | | 0.01 | | | 130 |
| 15-2 | 5 | | | 0.01 | | 135 |
| 15-3 | 5 | | | | 0.01 | 129 |
| 15-4 | | 5 | 0.01 | | | 125 |
| 15-5 | | 5 | | 0.01 | | 128 |
| 15-6 | | 5 | | | 0.01 | 124 |
| 15-7 | 5 | | | | | 116 |
| 15-8 | | 5 | | | | 112 |
| 15-9 | | | 0.01 | | | 104 |
| 15-10 | | | | 0.01 | | 105 |
| 15-11 | | | | | 0.01 | 106 |
| 15-12 | | | | | | 100 |

In the above table, the blank squares each indicate zero.

*1: Compound 1 refers to a jasmonic acid derivative of formula (1) wherein $R^1$ is —$C_5H_{11}$ and $R^2$ is —$CH(CH_3)_2$.

*2: Compound 2 refers to a jasmonic acid derivative of formula (1) wherein $R^1$ is —$C_5H_{11}$ and $R^2$ is —$C_4H_9$.

We claim:

1. A method of promoting plant growth which comprises applying to plants in the growth and development stage a plant growth promoter composition comprising an effective growth promoting 0.01 to 500 ppm amount of a jasmonic acid compound represented by the following formula:

(1)

wherein $R^1$ represents a pentyl group or a pentenyl group and $R^2$ represents a hydrogen atom or an alkyl group of 1 to 10 carbon atoms, and a carrier.

2. The method of promoting plant growth according to claim 1, wherein in the jasmonic acid compound of formula (1) $R^2$ is an alkyl group of 2–6 carbon atoms.

3. A method of promoting plant growth which comprises contacting plant seeds with a plant growth promoter composition comprising an effective growth promoting 0.01 to 500 ppm amount of a jasmonic acid compound represented by the following formula:

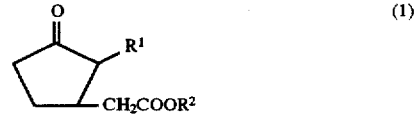

(1)

wherein $R^1$ represents a pentyl group or a pentenyl group and $R^2$ represents a hydrogen atom or an alkyl group of 1 to 10 carbon atoms, and a carrier.

4. The method of promoting plant growth according to claim 3, wherein in the jasmonic acid compound of formula (1) $R^2$ is an alkyl group of 2–6 carbon atoms.

5. A method for promoting plant growth of a plant which is a member selected from the group consisting of a root vegetable, a potato, a cereal, a fruit vegetable, a fruit tree, a flower, an ornamental plant and an industrial crop which comprises contacting the plant with a plant growth promoter composition comprising an effective growth promoting 0.01 to 500 ppm amount a jasmonic acid compound represented by the following formula:

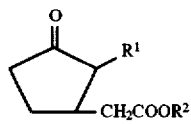
(1)

wherein $R^1$ represents a pentyl group or a pentenyl group and $R^2$ represents a hydrogen atom or an alkyl group of 1 to 10 carbon atoms, and a carrier.

6. The method of promoting plant growth according to claim 5, wherein in the jasmonic acid compound of formula (1) $R^2$ is an alkyl group of 2–6 carbon atoms.

7. A method for promoting plant growth which comprises contacting a portion of a plant which is selected from the plant group consisting of plant leaves, stems, roots, tubers, rhizomes, fruit and flower buds with a plant growth promoter composition comprising an effective growth promoting 0.01 to 500 ppm amount of a jasmonic acid compound represented by the following formula:

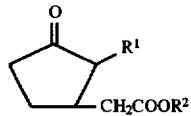
(1)

wherein $R^1$ represents a pentyl group or a pentenyl group and $R^2$ represents a hydrogen atom or an alkyl group of 1 to 10 carbon atoms, and a carrier.

8. The method of promoting plant growth according to claim 7, wherein in the jasmonic acid compound of formula (1) $R^2$ is an alkyl group of 2–6 carbon atoms.

9. A method for promoting plant growth of a plant which is a member selected from the group consisting of a root vegetable, a potato, a fruit vegetable, a fruit tree and a flower which comprises contacting the plant with an effective amount of the plant growth composition comprising an effective growth promoting 0.10 to 200 ppm amount of a jasmonic acid compound represented by the following formula:

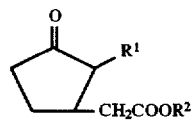
(1)

where $R^1$ is a member selected from the group consisting of pentyl group and pentenyl group and $R^2$ is a member selected from the group consisting of an alkyl group having 1 to 8 carbon atoms, and a plant growth promoter carrier.

10. The method for promoting plant growth of claim 9 wherein said plant is a root vegetable.

11. The method for promoting plant growth of claim 9 wherein said plant is a fruit vegetable.

12. The method for promoting plant growth of claim 9 wherein said plant is a fruit tree.

13. The method for promoting plant growth of claim 9, wherein said plant is a flower.

* * * * *